United States Patent [19]
Michelson

[11] Patent Number: 5,860,973
[45] Date of Patent: Jan. 19, 1999

[54] TRANSLATERAL SPINAL IMPLANT

[76] Inventor: Gary Karlin Michelson, 438 Sherman Canal, Venice, Calif. 90291

[21] Appl. No.: 741,301

[22] Filed: Oct. 30, 1996

Related U.S. Application Data

[63] Continuation of Ser. No. 479,596, Jun. 7, 1995, abandoned, which is a continuation-in-part of Ser. No. 394,836, Feb. 27, 1995.

[51] Int. Cl.$^6$ ................................................ A61B 17/56
[52] U.S. Cl. .............................................. 606/61; 606/72
[58] Field of Search ................................. 606/61, 72–78, 606/86, 87, 88; 623/16, 17

[56] References Cited

U.S. PATENT DOCUMENTS

| | | |
|---|---|---|
| 2,677,369 | 5/1954 | Knowles . |
| 3,298,372 | 1/1967 | Feinberg . |
| 3,867,728 | 2/1975 | Stubstad et al. . |
| 3,875,595 | 4/1975 | Froning . |
| 3,905,047 | 9/1975 | Long . |
| 4,070,514 | 1/1978 | Entherly et al. . |
| 4,259,072 | 3/1981 | Hirabayashi et al. . |
| 4,309,777 | 1/1982 | Patil . |
| 4,328,593 | 5/1982 | Sutter ........................................ 623/18 |
| 4,349,921 | 9/1982 | Kuntz ........................................ 623/17 |
| 4,501,269 | 2/1985 | Bagby ....................................... 623/18 |
| 4,535,485 | 8/1985 | Ashman et al. . |
| 4,545,374 | 10/1985 | Jacobson . |
| 4,553,273 | 11/1985 | Wu . |
| 4,599,086 | 7/1986 | Doty . |
| 4,636,217 | 1/1987 | Ogilvie et al. . |
| 4,714,469 | 12/1987 | Kenna . |
| 4,759,766 | 7/1988 | Buettner-Janz et al. . |
| 4,759,769 | 7/1988 | Hedman et al. . |
| 4,820,305 | 4/1989 | Harms et al. . |
| 4,848,327 | 7/1989 | Perdue . |
| 4,863,477 | 9/1989 | Monson . |
| 4,865,603 | 9/1989 | Noiles . |
| 4,877,020 | 10/1989 | Vich . |
| 4,904,261 | 2/1990 | Dove et al. . |
| 4,911,718 | 3/1990 | Lee ........................................... 623/17 |
| 4,936,848 | 6/1990 | Bagby . |
| 4,955,908 | 9/1990 | Frey et al. . |
| 4,961,740 | 10/1990 | Ray et al. . |
| 5,015,247 | 5/1991 | Michelson . |
| 5,015,255 | 5/1991 | Kuslich . |
| 5,026,373 | 6/1991 | Ray et al. . |
| 5,055,104 | 10/1991 | Ray . |
| 5,059,193 | 10/1991 | Kuslich . |
| 5,071,437 | 12/1991 | Steffee . |
| 5,123,926 | 6/1992 | Pisharodi . |
| 5,192,327 | 3/1993 | Brantigan . |
| 5,258,031 | 11/1993 | Salib et al. . |
| 5,263,953 | 11/1993 | Bagby . |
| 5,306,309 | 4/1994 | Wagner et al. . |
| 5,397,364 | 3/1995 | Kozak et al. . |
| 5,425,772 | 6/1995 | Brantigan . |
| 5,489,308 | 2/1996 | Kuslich et al. . |

FOREIGN PATENT DOCUMENTS

| | | |
|---|---|---|
| 0 260 044 | 3/1988 | European Pat. Off. . |
| 0 179 695 | 4/1986 | France . |

Primary Examiner—Michael Buiz
Assistant Examiner—Kevin Truong
Attorney, Agent, or Firm—Lewis Anten, Esq.; Amedeo Ferraro, Esq.

[57] ABSTRACT

An oversized spinal implant for translateral insertion into the disc space between two vertebrae a length that is greater than one half of the transverse width of the vertebrae and is greater than the depth of the vertebrae. The translateral implant of the present invention has a height that is greater than the height of the disc space between two adjacent vertebrae so as to engage both of the vertebrae. The width of the implant need be only slightly less than the depth of the vertebrae themselves. The translateral spinal fusion implant of the present invention has more surface area of contact and thus permits greater stability so as to withstand torque, and in the case of a threaded implant, increases the depth which any threads are able to penetrate the vertebrae.

73 Claims, 8 Drawing Sheets

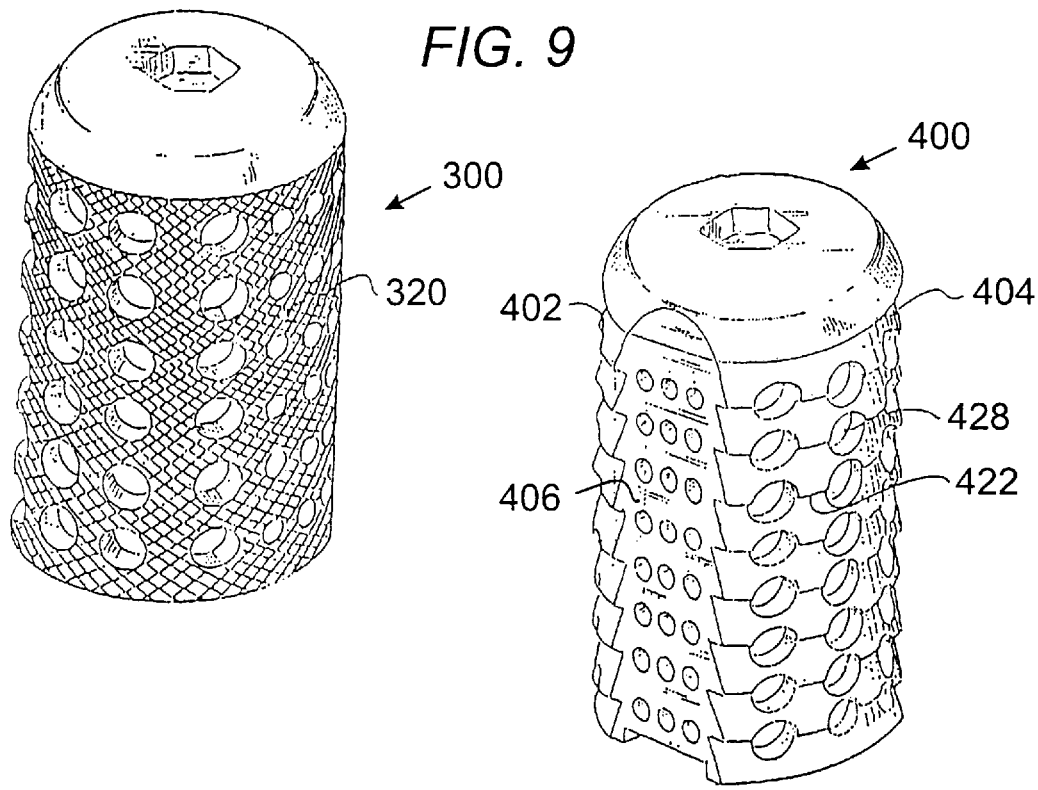
FIG. 9
FIG. 10
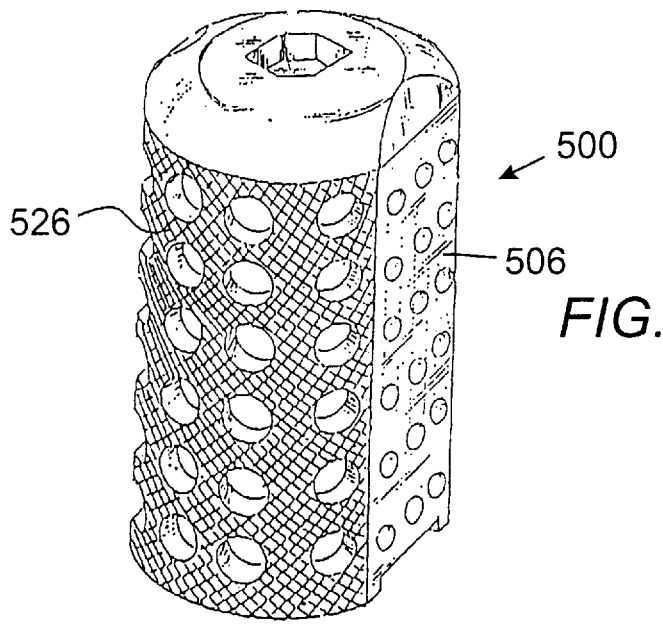
FIG. 11

FIG. 15
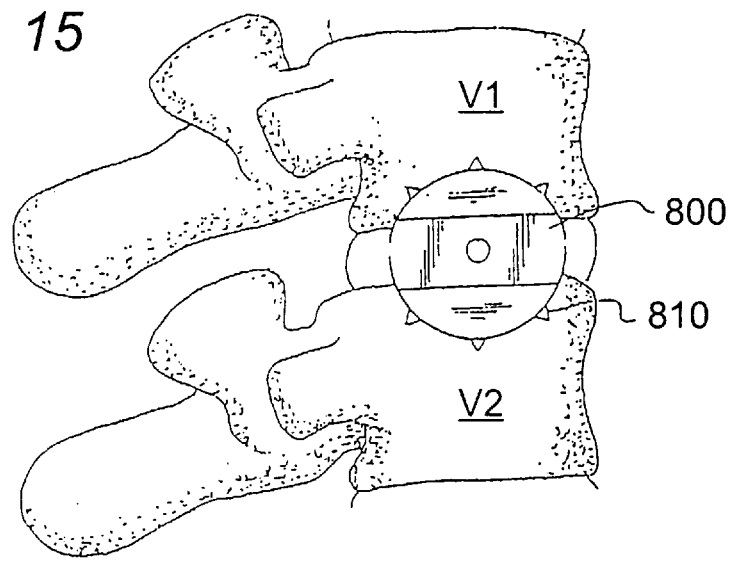
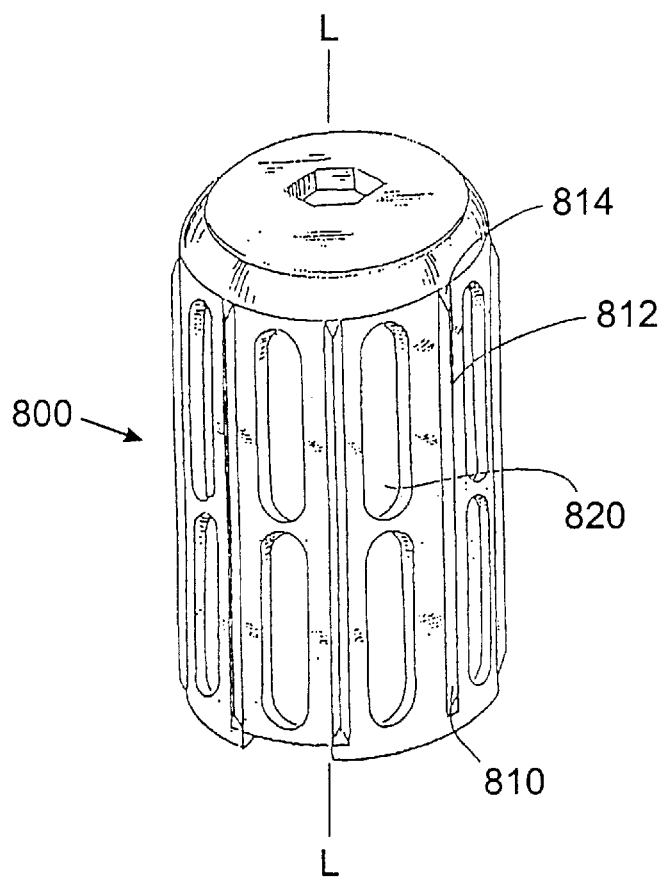
FIG. 15b

TRANSLATERAL SPINAL IMPLANT

RELATED APPLICATIONS

This is a continuation of the application Ser. No 08/479,596 filed on Jun. 7, 1995, now abandoned, which is a continuation in part of application Ser. No. 08/394,836 entitled IMPROVED METHODS AND INSTRUMENTATION FOR THE SURGICAL CORRECTION OF HUMAN THORACIC AND LUMBAR SPINAL DISEASE FROM THE LATERAL ASPECT OF THE SPINE, filed on Feb. 27, 1995 now pending, incorporated herein by reference.

BACKGROUND OF THE INVENTION

1. Field of the Invention

This invention relates generally to spinal fusion implants, and more particularly to spinal fusion implants for insertion from the side of a patient (translateral) across the transverse width of the spine and between two adjacent vertebrae.

2. Description of the Related Art

In the past, spinal fusion implants have been inserted only from either an anterior or posterior direction, from the front or the back of the patient. Such implants are well known in the art and may have cylindrical, rectangular and other shapes. In the past, Cloward, Wilterberger, Crock, Viche, Bagby, Brantigan, and others have taught various methods involving the drilling of holes across the disc space between two adjacent vertebrae of the spine for the purpose of causing an interbody spinal fusion. Cloward taught placing a dowel of bone within that drilled hole for the purpose of bridging the defect and to be incorporated into the fusion. Viche taught the threading of that bone dowel. Bagby taught the placing of the bone graft into a metal bucket otherwise smooth on its surface, except for rows of radially placed holes communicative to the interior of the basket and to the bone graft. The Bagby device was disclosed as capable of being used in a horse. Brantigan taught the use of inert blocks preferably made of metal and having that metal at its external surface imitate the porosity of bone. Brantigan theorized that the bone dowel could be replaced entirely with a metal plug that, while not itself active in the fusion, would nevertheless serve to support the vertebrae from within the disc space while allowing fusion to occur around it.

U.S. Pat. No. 3,844,601 issued to Ma et al. on Nov. 19, 1974, teaches a method and instrumentation for preparing rectangular spaces across the disc space into the adjacent vertebrae and for preparing a rectangular graft of the bone itself that is inserted in the rectangular spaces.

U.S. Pat. No. 4,743,256 issued to Brantigan on May 10, 1988 teaches the use of an inert artificial spacer in the shape of a rectangle in place of using a rectangular bone graft as taught by Ma et al.

U.S. Pat. No. 4,878,915 issued to Brantigan on Nov. 7, 1989, teaches the use of fully cylindrical inert implants for use in interbody spinal fusion. Such implants do not participate in the bone fusion process but act as inert spacers and allow for the growth of bone to the outer surfaces of the implants.

U.S. Pat. No. 4,834,757 issued to Brantigan on May 30, 1989, teaches a rectangular shaped, hollow spinal fusion implant for use in lieu of a rectangular bone graft or Brantigan's earlier artificial inert spacer.

However, all of the prior implants have been inserted from either the front or the back of the patient. As a result, the spinal fusion implants of the past were necessarily limited in size to the dimensions of the vertebrae relative to the direction in which the implants were inserted. For example, the maximum possible length for an implant that is inserted from either the front or the back of the patient is limited to the depth of the vertebrae, the depth of a vertebrae being the dimension of the vertebrae measured from the anterior end to the posterior end of the vertebrae. It was not previously possible to insert an implant that had a length that was greater than the depth of the vertebrae from front to back as such an implant would protrude from either the anterior or posterior aspect of the spine resulting in great harm to the patient.

In U.S. Pat. No. 5,015,247 to Michelson, a cylindrical threaded implant is described for insertion across the disc space between two adjacent vertebrae. Such an implant was disclosed as being inserted either from the front of the patient or from the back and has a diameter larger than the disc space so that it engages both of the adjacent vertebrae.

The maximum diameter possible with a cylindrical implant that is inserted from the front or the back of the patient is limited by at least two factors. The first factor limiting the diameter of a cylindrical implant is realized when an attempt is made to use a single, centrally placed implant from either the front or the back of the patient. Such an implant must be large enough to occupy a sufficient portion of the transverse width of the disc space to promote firm stability. The use of an implant that is placed in the disc space to stabilize the two adjacent vertebrae requires that the vertebrae be stable when the implant is in place, otherwise there will not be any bone bridging between the implant and the vertebrae. If a single implant is used in the center of the disc space, inherent instability is created, as the vertebrae are generally free to rock back and forth over the implant which serves as a fulcrum. However, to achieve the required stability, it would be necessary to use the widest possible implant and the excursion of such a large single implant into the adjacent vertebrae would be so severe that the two vertebrae would be virtually cut in half.

The second factor which limits the diameter size of a cylindrical implant is in the situation where two cylindrical implants are implanted from either the front or the back of the patient and placed side-by-side across a disc space and into the two adjacent vertebrae in an attempt to gain stability while avoiding the problems of the single implant. Such implants require a diameter that is sufficiently large to penetrate into and significantly engage each of the adjacent vertebrae yet the diameter may not be so large that it is no longer possible to place two such implants side-by-side and to still have them contained within the transverse width of the spine.

The use of multiple implants requires that the implants be small enough so as to fit into the same limited spinal width. These implants being of smaller diameter as limited by the need to place more than one within the width of the spine then penetrate only minimally into the depth of the vertebral bone.

Also, the insertion of multiple implants requires multiple procedures, essentially a duplication of any procedure done on one side of the center line must also be performed on the other side of the center line.

Therefore, there exists a need for a spinal fusion implant that is inserted from the translateral approach to the spine that is capable of stabilizing the vertebrae adjacent to such an implant in order to permit bone bridging between the vertebrae and the implant to ultimately achieve fusion of the adjacent vertebrae.

SUMMARY OF THE INVENTION

The present invention discloses a spinal fusion implant that is inserted from the side of the patient, herein referred to as the translateral approach to the spine. The translateral spinal fusion implant of the present invention is inserted into the spine of a patient across the transverse width of the vertebrae to be fused. The transverse width of a vertebra is measured from one lateral aspect of the spine to the opposite lateral aspect. The depth of a vertebra is measured from the anterior aspect to the posterior aspect of the spine.

As the translateral spinal fusion implant of the present invention is inserted substantially along the transverse width of the vertebrae or at a slight angle to the vertebrae, it has a different structural configuration as compared to spinal implants for insertion from either the front or the back of the patient, as such implants are necessarily limited by the depth, measured from front to back of the vertebrae.

In one embodiment of the translateral spinal fusion implant of the present invention, the implant is dimensioned to fit within a bore created across the disc space and into the adjacent vertebrae. Such an implant may be substantially cylindrical and has an outer surface comprising bone engaging means for engaging the implant to the adjacent vertebrae. In this embodiment, for the lumbar spine, the translateral spinal fusion implant of the present invention has a length that is greater than one half of the transverse width of the vertebrae and is greater than the depth of the vertebrae. The translateral implant of the present invention has a height that is greater than the height of the disc space between two adjacent vertebrae so as to engage both of the vertebrae. The width of the implant need be only slightly less than the depth of the vertebrae themselves.

In another embodiment of the present invention, the translateral spinal fusion implant of the present invention is dimensioned to fit within the disc space created by the removal of disc material between two adjacent vertebrae. Such an implant is inserted from the translateral approach to the spine and has a length that is substantially greater than the depth of the vertebrae and a width that approximates the depth of the vertebrae. The height of such an implant is approximately the same height of the normal height of the disc space between two adjacent vertebrae and may be wedged so as to reproduce anatomic lordosis. The upper and lower surfaces of such an implant may be contoured so as t conform to the shape of the disc space and the adjacent vertebral endplate surfaces.

The dimensions of the translateral spinal fusion implant of the present invention permits a single implant to be inserted by a single procedure into the spine and to engage more of the adjacent vertebrae. As a result, the translateral spinal fusion implant of the present invention has more surface area of contact and thus permits greater stability so as to withstand torque, and in the case of a threaded implant, increases the depth which any threads are able to penetrate the vertebrae.

The translateral implants of the present invention are safer to use than implants inserted from the front or the back as the aorta and vena cava lie anterior to the spine and the dural sac and nerves posteriorly, all of which structures are simply avoided in the lateral approach.

The translateral spinal fusion implant of the present invention may be inserted into the disc space through a hollow tube which is engaged to the lateral aspect of the spine through a lateral, anterior, or anterolateral incision making the procedure safe and simple.

The translateral spinal fusion implant of the present invention may comprise at least in part fusion promoting and/or bioactive materials for active participation of the implant in the spinal fusion process.

OBJECTS OF THE PRESENT INVENTION

It is an object of the present invention to provide a spinal fusion implant that may be inserted from a translateral approach to the spine.

It is another object of the present invention to provide a spinal fusion implant that is safer to use than the implants of the past.

It is another object of the present invention to provide a spinal fusion implant that is easier to insert into the spine.

It is a further object of the present invention to provide a spinal fusion implant that provides greater stability of the vertebrae being fused.

It is yet another object of the present invention to provide a spinal fusion implant that is less likely to fail.

It is another object of the present invention to provide a spinal fusion implant that is more deeply embedded into the adjacent vertebrae.

These and other objects of the present invention will become apparent from a review of the accompanying drawings and the detailed description of the drawings.

BRIEF DESCRIPTION OF THE DRAWINGS

FIG. 9 is a perspective view of an alternative embodiment of the spinal fusion implant of the present invention having a knurled surface for engaging the vertebrae.

FIG. 10 is a perspective view of an alternative embodiment of the spinal fusion implant of the present invention having ratchetings for engaging the vertebrae and a flattened side.

FIG. 11 is a perspective view of an alternative embodiment of the spinal fusion implant of the present invention having a knurled surface for engaging the vertebrae and a flattened side.

FIG. 14 is a perspective view of an alternative embodiment of the spinal fusion implant of the present invention having longitudinal splines for engaging the vertebrae and openings in the form of vertical slots.

FIG. 15 is elevational view of the lateral aspect of the spinal column having the spinal fusion implant of FIG. 14 inserted from the lateral aspect along the transverse width of the vertebrae into a hole created across the disc space and into two adjacent vertebrae.

DETAILED DESCRIPTION OF THE DRAWINGS

Figure 1:
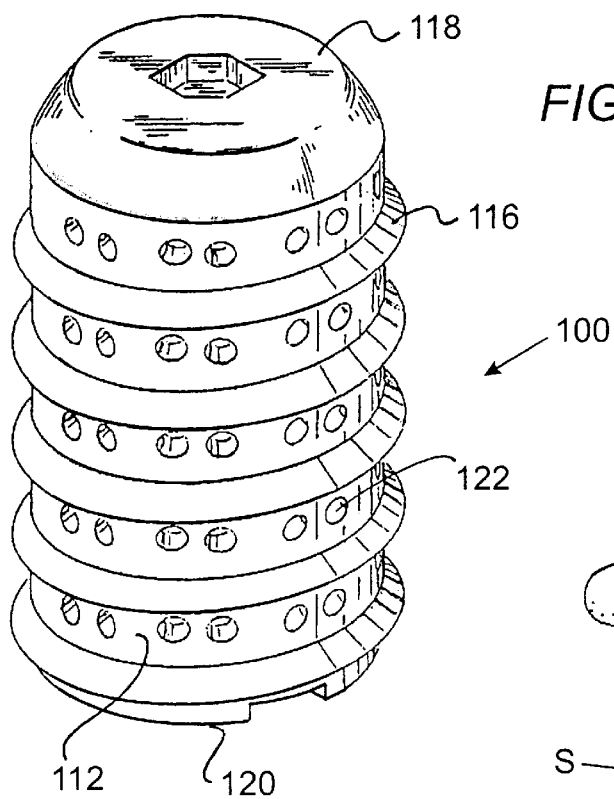
FIG. 1 is a perspective side view of the translateral spinal fusion implant of the present invention having an external thread for engaging the bone of two adjacent vertebrae.

Referring to FIGS. 1–5, an embodiment of the translateral spinal fusion implant of the present invention, generally referred to by numeral 100, is shown. The spinal fusion implant 100 has a substantially cylindrical configuration having an outer wall 112 surrounding an internal chamber 114 for holding fusion promoting material. The exterior of the spinal fusion implant 100 comprises an external thread 116 suitable for engaging the vertebrae of the spine to stabilize the spinal fusion implant 100 across the disc space and into adjacent vertebrae once surgically implanted. The spinal fusion implant 100 has a removable cap 118 at one end which provides access to the internal chamber 114 and has an insertion end 120 adapted to engage insertion instrumentation.

The cap 118 is removable to provide access to the internal chamber 114, such that the internal chamber 114 can be filled and hold any natural or artificial osteoconductive, osteoinductive, osteogenic, or other fusion enhancing material. Some examples of such materials are bone harvested from the patient, or bone growth inducing material such as, but not limited to, hydroxyapatite, hydroxyapatite tricalcium phosphate; or bone morphogenic protein. The cap 118 and/or the spinal fusion implant 100 itself is made of material appropriate for human implantation such as titanium and/or may be made of, and/or filled and/or coated with a bone ingrowth inducing material such as, but not limited to, hydroxyapatite or hydroxyapatite tricalcium phosphate or any other osteoconductive, osteoinductive, osteogenic, or other fusion enhancing material.

The outer wall 112 comprises openings 122 which may be closed wells or openings communicating into the internal chamber 114 to permit bone ingrowth into the chamber 114.

Figure 2:
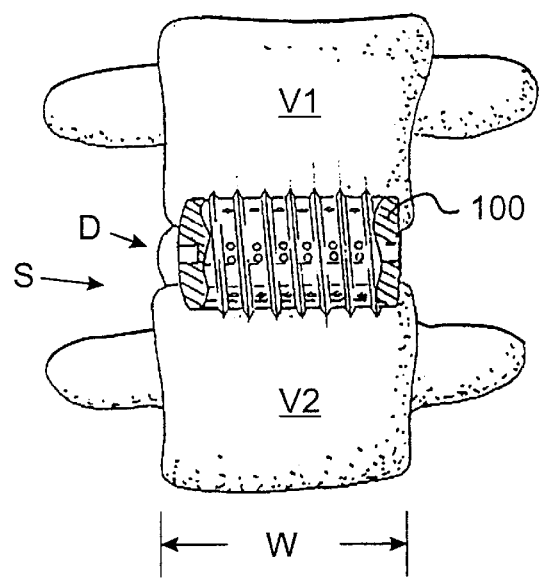
FIG. 2 is an elevational view of the anterior aspect of a segment of the spinal column with the spinal fusion implant of FIG. 1 inserted from the lateral aspect along the transverse width of the vertebrae.

Referring specifically to FIG. 2, an elevational view of the anterior aspect of a segment of the spinal column S with the spinal fusion implant 100 inserted from the lateral aspect of the spinal column S into a hole bored into the adjacent vertebrae $V_1$ and $V_2$ across the disc space D. The spinal fusion implant 100 is inserted along the transverse width W of the adjacent vertebrae $V_1$ and $V_2$ such that the spinal fusion implant 100 extends translaterally in the direction from one lateral aspect of the vertebrae to the opposite lateral aspect of the vertebrae.

Figure 3:
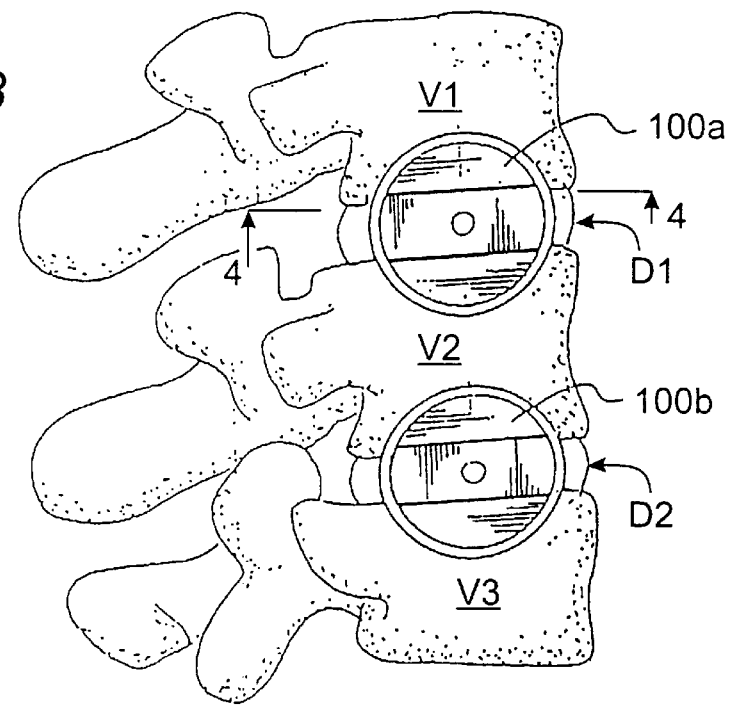
FIG. 3 is an elevational view of the lateral aspect of a segment of the lumbar spine with a first spinal fusion implant of the present invention inserted from the lateral aspect into a hole drilled across a first disc space and into two adjacent vertebrae, and a second spinal fusion implant of the present invention inserted from the lateral aspect into a second hole drilled across a second disc space and into two adjacent vertebrae.

Referring to FIG. 3, an elevational view of the lateral aspect of a segment of the lumbar spine S is shown with a first implant 100a, identical to spinal fusion implant 100, inserted from the lateral aspect into a hole bored across a first disc space $D_1$ and into two adjacent vertebrae $V_1$ and $V_2$, and a second implant 100b, identical to spinal fusion implant 100, inserted from the lateral aspect into a second hole bored across a second disc space $D_2$ and into two adjacent vertebrae $V_2$ and $V_3$.

The translateral implants of the present invention are inserted by the translateral method disclosed in copending application Ser. No. 08/394,836 entitled IMPROVED METHODS AND INSTRUMENTATION FOR THE SURGICAL CORRECTION OF HUMAN THORACIC AND LUMBAR SPINAL DISEASE FROM THE LATERAL ASPECT OF THE SPINE, filed on Feb. 27, 1995, which is incorporated herein by reference. The tanslateral implants of the present invention may be made of an artificial material.

Figure 4:
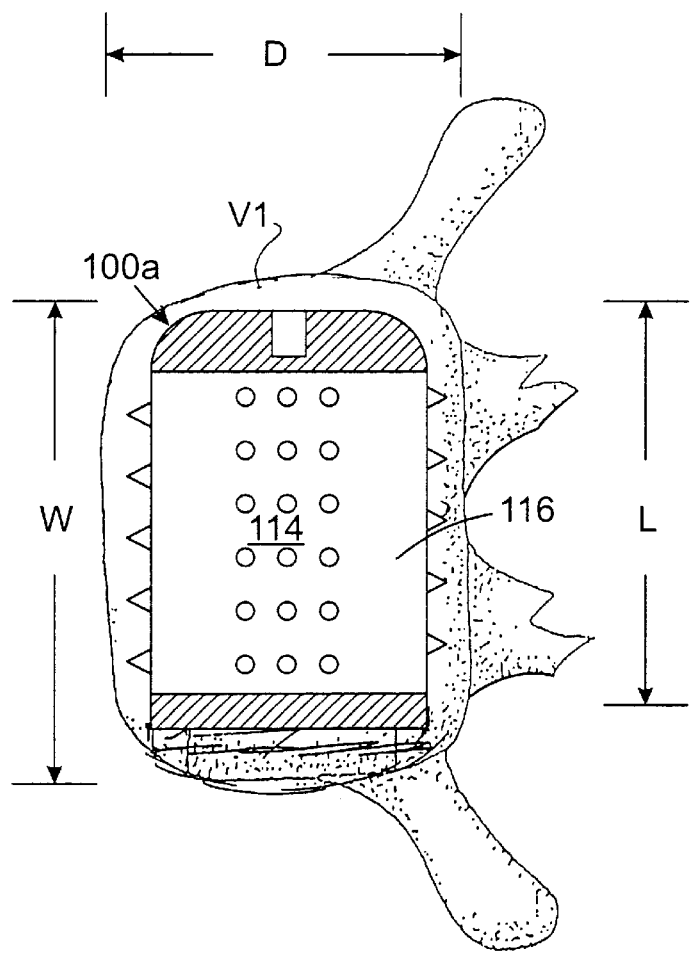
FIG. 4 is top sectional view along lines 4—4 of FIG. 3 showing the area of contact of the spinal fusion implant of the present invention and the vertebra.

Referring to FIG. 4, a top sectional view along lines 4—4 of FIG. 3 is shown illustrating the area of contact of the implant 100a and the vertebra $V_1$. The vertebra $V_1$ has a depth D measured from the anterior to posterior aspect of the spine, and a transverse width W measured from one lateral aspect to the opposite lateral aspect of the vertebra $V_1$. The implant 100a has a length L that is substantially greater than the depth D of the vertebra $V_1$ such that the implant 100a may extend substantially across the transverse width W of the vertebra $V_1$. In the preferred embodiment, the implant 100a has a length L that is greater than one half the transverse width W of the vertebrae and has a diameter of a sufficiently large size that approximates the depth D of the vertebra $V_1$. As a result of the large length and diameter of the implant 100a, a large surface area of contact between the implant 100a and the vertebrae $V_1$ is possible creating a highly stable construct. The implant 100a has a much greater surface area of contact with the vertebra $V_1$ than was previously possible with implants that are inserted from the front or the back of the spine.

As described above in the Background of the Invention, a centrally placed single implant from either the front or the back of the patient must be large enough to occupy a sufficient portion of the transverse width W of the vertebrae to promote firm stability. However, the vertical height of such an implant and excursion into the adjacent vertebrae would be so severe that if any two consecutive disc spaces were to be operated upon, the vertebra in between the disc spaces would be cut in half. Therefore it has been the practice to use multiple implants, one on each side of the center line (mid-saggital axis) of the vertebrae, thereby providing a greater degree of stability.

Figure 5:
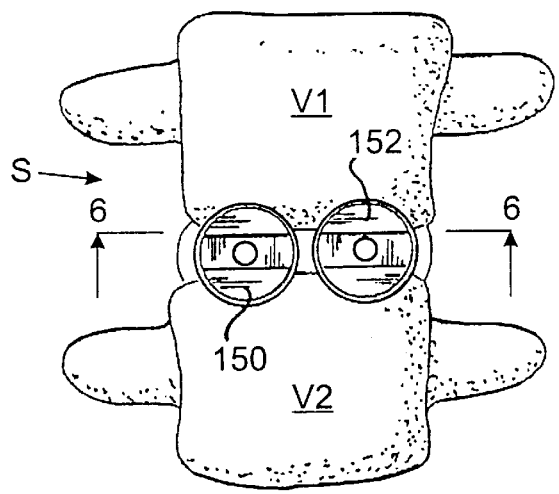
FIG. 5 is an anterior elevational view of a segment of the lumbar spine with two cylindrical implants inserted from the anterior of the spine into holes drilled across the same disc space and into two adjacent vertebrae.

Referring to FIG. 5, an anterior elevational view of a segment of the lumbar spine S is shown with two cylindrical implants 150 and 152 inserted from the anterior aspect of the spine S into holes drilled across the same disc space D and into two adjacent vertebrae $V_1$ and $V_2$.

Figure 6:
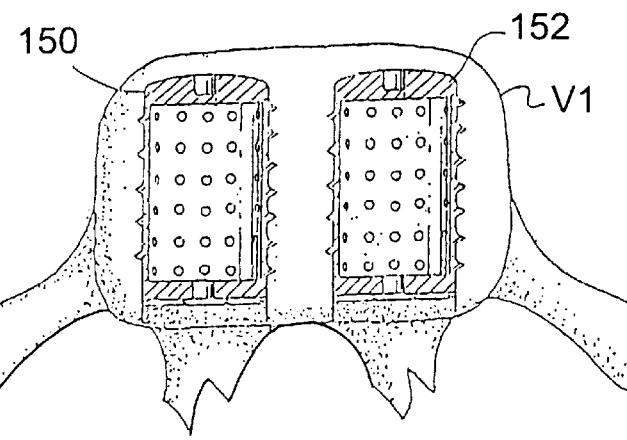
FIG. 6 is sectional view along lines 6—6 of FIG. 5 showing the area of contact between the two implants of FIG. 5 and the vertebra.

Referring to FIG. 6, sectional view along lines 6—6 of FIG. 5 illustrating the area of contact between the two implants 150 and 152 inserted from the anterior aspect of the spine and the vertebra $V_1$ is shown. As can be seen from FIG. 6, the surface area of the two spinal implants 150 and 152 in contact with the vertebra $V_1$ is substantially less than that of a single translateral spinal fusion implant 100 that is inserted across the transverse width W of the vertebra $V_1$. As a result, a more stable construct is achieved with the translateral spinal fusion implant 100 of the present invention than was previously possible with implants that are inserted from either the front or the back of the patient promoting from stability of the fusion construction.

In the preferred embodiment, the spinal fusion implant 100 of the present invention has an overall length in the range of 35 mm to 50 mm, with 38–44 mm being preferred, and a maximum diameter in the range of 22 mm to 30 mm, with 24–26 mm being preferred when inserted in the lumbar spine. In the thoracic spine such implants would have a length in the range of 12–30 mm, and a maximum diameter in the range of 14–26 mm, with the preferred diameter being 20 mm.

Figure 7:
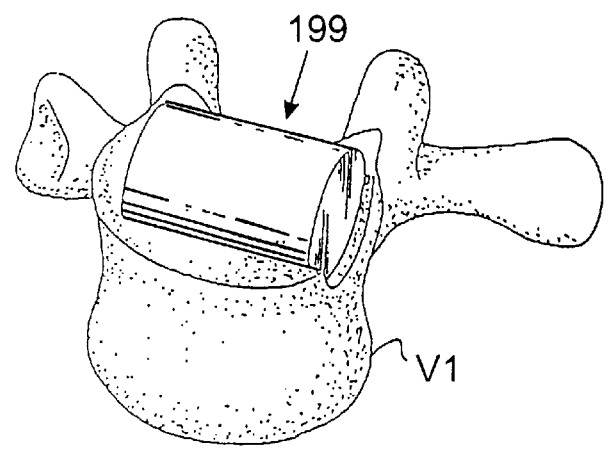
FIG. 7 is a anterior perspective view of a single vertebra and an alternative embodiment of the spinal fusion implant of the present invention in the form of a dowel inserted translaterally into a hole drilled across a disc space and into the vertebra along the transverse width of the vertebra.

Referring to FIG. 7, an anterior perspective view of a single vertebra $V_1$ and an alternative embodiment of the translateral spinal fusion implant of the present invention, generally referred to by the numeral 199, is shown. The spinal fusion implant 199 is a dowel inserted into a hole drilled across a disc space and into the vertebra $V_1$ along the transverse width of the vertebra $V_1$. The spinal fusion implant 199 has the same dimensions as the spinal fusion implant 100 described above. The spinal fusion implant 199 can be made of any material suitable for human implantation may comprise fusion promoting and/or bioactive material to actively participate in the spinal fusion process. The implant 199 can be made of a porous, and/or mesh-like, and/or cancellous material, or any other material suitable for the described purpose.

Figure 8:
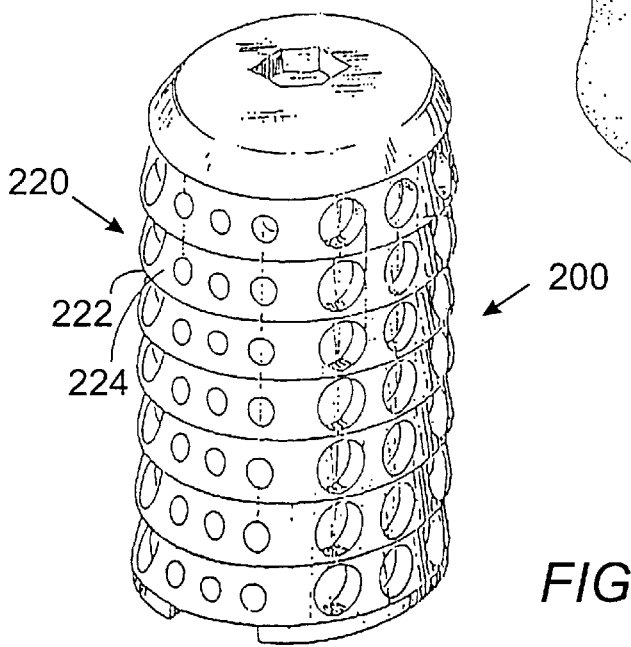
FIG. 8 is a perspective view of an alternative embodiment of the spinal fusion implant of the present invention having ratchetings for engaging the vertebrae.

Referring to FIG. 8, an alternative embodiment of the translateral spinal fusion implant of the present invention, is shown and generally referred to by the numeral 200. The spinal fusion implant 200 has a substantially cylindrical configuration having a thin outer wall 212 surrounding an internal chamber 214. The exterior of the spinal fusion implant 200 comprises surface roughenings that provide a surface suitable for engaging the bone of the vertebrae to stabilize the spinal fusion implant 200 across the disc space and into the adjacent vertebrae once surgically implanted. The surface roughenings comprise a plurality of ratchetings 220 along the circumference of the spinal fusion implant 200. Each of the plurality of ratchetings 220 has a bone engaging edge 222 and an angled segment 224.

The spinal fusion implant 200 is implanted into a cylindrical bore derived across the disc space and into two adjacent vertebrae. The spinal fusion implant 200 may be pushed into the cylindrical bore across the disc space by direct, linear advancement since it requires no thread to pull it forward through the spine. As no torque is required to advance the spinal fusion implant 200 there is no minimum requisite height of the surface roughenings.

The ratchetings 220 may face in one direction, the direction in which the spinal fusion implant 200 is inserted, and function to prevent the spinal fusion implant 200 from backing out of the disc space in a direction opposite to the direction of insertion once inserted between the two adjacent vertebrae. The ratchetings 220 urge the spinal fusion implant 200 forward against the unremoved bone of the vertebrae. Since implants generally want to back out along the same path in which they are inserted, the ratchetings 220 tend to urge the spinal fusion implant 200 forward against the solid unremoved bone at the end of the cylindrical bone, further resisting dislodgement and controlling motion resulting in an exceedingly stable implantation.

The spinal fusion implant 200 has an engagement means at one end for engaging a driver instrument for intimately engaging and binding the implant 200 and the driver instrument together. Once affixed to the implant driver instrument, the spinal fusion implant 200 may be then introduced through a hollow cylindrical tube and driven into the cylindrical hole that has been drilled across the disc space. The implant driver instrument may then be impacted by a mallet, or similar device, to linearly advance the spinal fusion implant 200 across the disc space. Once the spinal fusion implant 200 is inserted across the disc space, the ratchetings 220, engage the bone of the vertebrae and the implant driver instrument is detached from the spinal fusion implant 200.

Referring to FIG. 9, an alternative embodiment of the spinal fusion implant of the present invention generally referred to by the numeral 300 is shown. The spinal fusion implant 300 has a substantially cylindrical configuration having surface roughenings for stabilizing the implant 300 within the intervertebral space D. The surface roughenings comprise a surface knurling 320 such as, but not limited to, the diamond-shaped bone engaging pattern shown in FIG. 9. The spinal fusion implant 300 may have surface knurling 320 throughout the entire external surface of the spinal fusion implant 300, throughout only a portion of the external surface, or any combination thereof, without departing from the scope of the present invention. In those circumstances where there is no undrilled bone in the disc space forward of the spinal fusion implant 300 to resist further forward advancement of the implant, surface knurling 320 is preferred as it produces an exceedingly high interference fit with the bone of the vertebrae and resists motion equally in all directions and without the tendency to urge itself forward.

Referring to FIG. 10, an alternative embodiment of the spinal fusion implant of the present invention is shown and is generally referred to by the numeral 400. The spinal fusion implant 400 has a similar configuration to that of the spinal fusion implant 200, except that it comprises a partially cylindrical member having arcuate portions 402 and 404 which are arcs of the same circle with portions of its outer wall that are flattened so as to present a first flat side 406. Alternatively, the implant 400 may have a second flat side that is diametrically opposite to the first flat side 406. The spinal fusion implant 400 is substantially the same as the spinal fusion implant 200, except that the openings 428 are positioned on the ratcheting 420 such that the openings 428 are positioned between the bone engaging edges 422 and are not bisected by the bone engaging edges 422.

Referring to FIG. 11, an alternative embodiment of the spinal fusion implant of the present invention is shown and generally referred to by the numeral 500. The spinal fusion implant 500 is substantially identical to the spinal fusion implant 400 described above except that in place of ratchetings 420, it has surface knurling 520. The surface knurling 520 assists in the retaining of the spinal fusion implant 500 once it is inserted across the disc space between two adjacent vertebrae. It is recognized that the surface knurling 520 of the implant 500 may be combined with any of a number of other surface roughenings such as, but not limited to, ratchetings to assist in retaining the spinal fusion implant 500 across the disc space.

Figure 12:
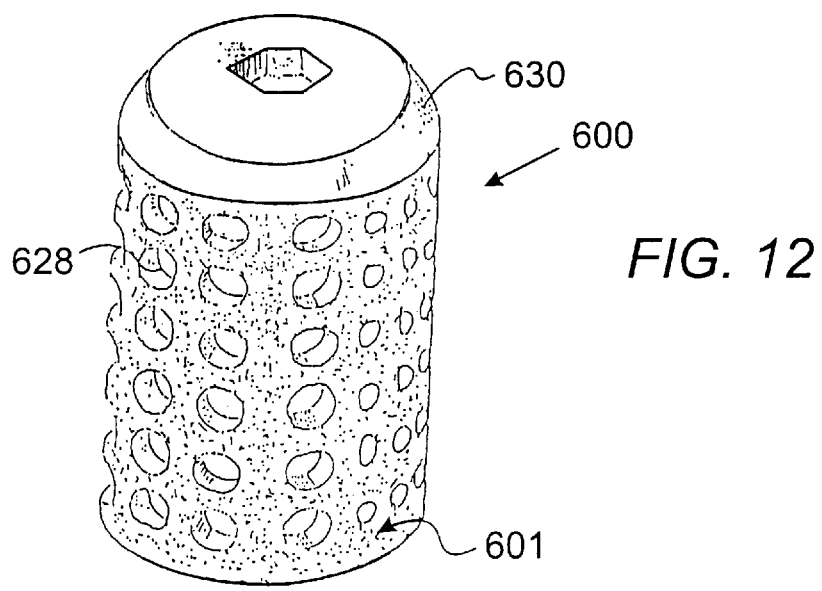
FIG. 12 is a perspective view of an alternative embodiment of the spinal fusion implant of the present invention having a blasted surface for engaging the vertebrae.

Referring to FIG. 12, an alternative embodiment of the spinal fusion implant of the present invention generally referred to by the numeral 600 is shown. The spinal fusion implant 600 has the same structure as the spinal fusion implant 300 described above but instead of knurling 320 has a different surface roughening. The spinal fusion implant 600 has a surface roughening comprising of a blasted external surface 601 which may be stippled to provide an engagement surface for the vertebrae when inserted across the disc space. The spinal fusion implant has a plurality of openings 628, a removable cap 630 for accessing an internal chamber.

Figure 13:
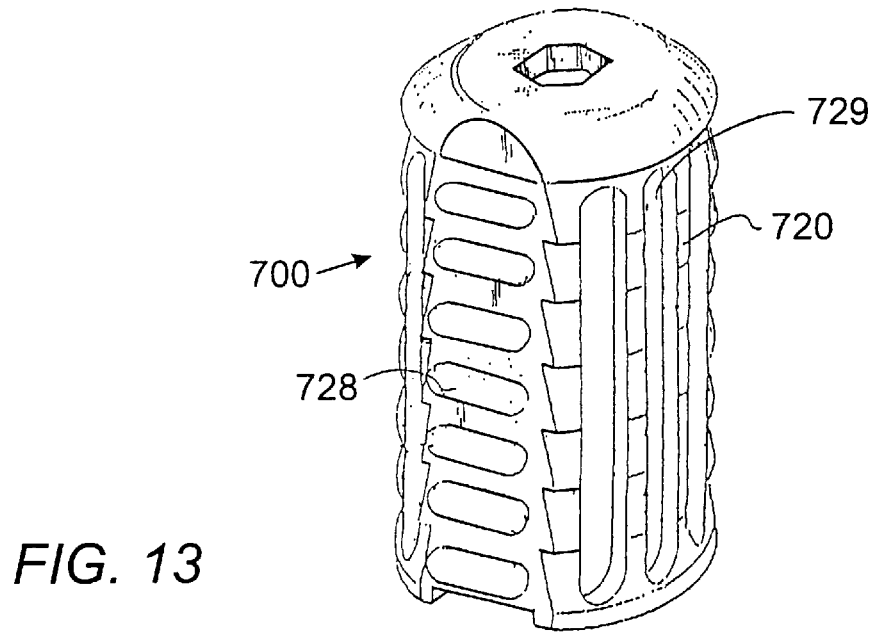
FIG. 13 is a perspective view of an alternative embodiment of the spinal fusion implant of the present invention having ratchetings for engaging the vertebrae with openings in the form of vertical and horizontal slots.

Referring to FIG. 13, an alternative embodiment of the spinal fusion implant of the present invention generally referred to by the numeral 700 is shown. The spinal fusion implant 700 is similar to spinal fusion implant 400 described above except that it has openings in the form of horizontal slots 728 on the flat side 706 and vertical slots 729 on the cylindrical portion of the spinal fusion implant 700. The spinal fusion implant 700 has ratchetings 720 for engaging the bone of the vertebrae similar to the ratchetings 220 described above.

It is appreciated that the spinal fusion implants of the present invention may include any and all surface roughening configurations that either increase the surface area or interference fit of the implant and the vertebrae. It is appreciated that the ratchetings described above for the various embodiments of the spinal fusion implants of the present invention may also comprise a knurled or other surface roughenings in combination with the ratchetings to further enhance the retention of the spinal fusion implant across the disc space once inserted.

Referring to FIG. 14, an alternative embodiment of the spinal fusion implant of the present invention is shown and generally referred to by the numeral 800. The spinal fusion implant 800 is similar in configuration to the spinal fusion implant 100 discussed above. However, instead of an external thread, the spinal fusion implant 800 has a plurality of longitudinal splines 810 along its external surface. The splines 810 are parallel to the central longitudinal axis L of the implant 800 in the direction of insertion of the implant 800. The splines 810 have a sharp edge 812 and a sharpened leading end 814 to facilitate insertion of the spinal fusion implant 800 into the adjacent vertebrae. Located between the splines 812 are a plurality of slots 820 that allow bone growth into the implant and into the internal chamber of the implant 800 during spinal fusion.

Referring to FIG. 15, the spinal fusion implant 800 is shown inserted from the lateral aspect of the spine into a bore created across the disc space D and into the adjacent vertebrae $V_1$ and $V_2$ along the transverse width of the vertebrae $V_1$ and $V_2$. The spinal fusion implant 800 is pushed into place by linear advancement such that the splines 810 engage a portion of each of the adjacent vertebrae $V_1$ and $V_2$. The splines 810 function to engage the vertebrae $V_1$ and $V_2$ and stabilize the spinal fusion implant 800 once implanted. The splines 810 are oriented longitudinally with respect to the spinal fusion implant 800 to prevent any dislodgement of the spinal fusion implant 800 from between the vertebrae $V_1$ and $V_2$ as result of anterior to posterior motion of the spine. It is appreciated that the number of splines 810 and the configuration of the splines 810 can vary depending on the size of the spinal fusion implant 800 being implanted.

Figure 16:
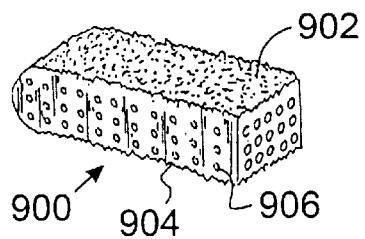
FIG. 16 is a perspective side view of an alternative embodiment of the spinal fusion implant of the present invention.

Referring to FIG. 16, an alternative embodiment of the spinal fusion implant of the present invention is shown and generally referred to by the numeral 900. The spinal fusion implant 900 differs from the implants described above in that it is inserted in the disc space D between the adjacent vertebrae of the spine and not into a cylindrical bore created across the disc space. Therefore, the spinal fusion implant 900 does not require the removal of any portion of bone from the adjacent vertebrae as the spinal fusion implant 900 fits within the natural disc space between the adjacent vertebrae. However, the removal of at least a portion of the disc material present between the adjacent vertebrae is required for proper insertion.

The spinal fusion implant 900 comprises a rectangular block 901 having a top surface 902 and a bottom surface 904 for engaging the adjacent vertebrae and may be flat or may conform at least in part. The top and bottom surfaces 902 and 904 may comprise any of the surface roughenings described herein for engaging the bone of the adjacent vertebrae to promote firm stability. The spinal fusion implant 900 may be solid or hollow at least in part and have a plurality of openings 906 to allow bone ingrowth. The openings 906 may be present on all surfaces of the implant 900 and may either pass through the entire implant 900, or may be closed bottom wells for holding fusion promoting materials.

Figure 17:
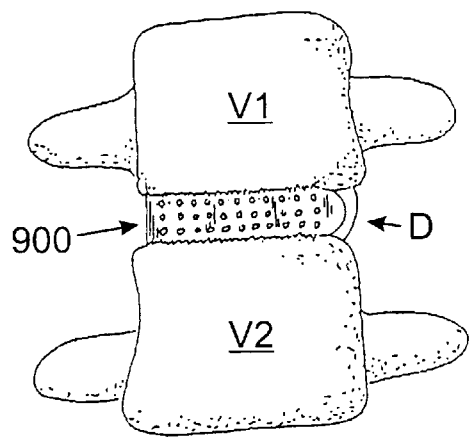
FIG. 17 is a elevational anterior view of a segment of the spinal column having the spinal fusion implant of FIG. 16 inserted from the lateral aspect in the disc space between two adjacent vertebrae along the transverse width of the vertebrae.

Referring to FIG. 17, the spinal fusion implant 900 is shown implanted from the lateral aspect of the spine in the disc space D between two adjacent vertebrae V, $V_1$ and $V_2$ along the transverse width of the adjacent vertebrae $V_1$ and $V_2$. The spinal fusion implant 900 has a height that is substantially equal to the height of the disc space D, a length that is greater than one half the transverse width W of the vertebrae and a width that approximates the depth of the vertebrae.

In the preferred embodiment, the spinal fusion implant 900 has a height in the range of 8 mm to 16 mm, with the preferred height being 10–12 mm; a width in the range of 24 mm to 32 mm, with the preferred width being 26 mm; and a length in the range of 32 mm to 50 mm, with 42 mm being the preferred length.

Figure 18:
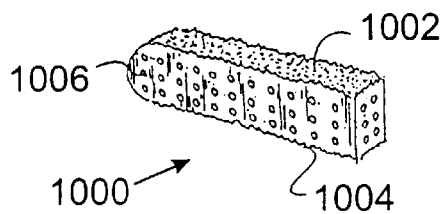
FIG. 18 is a perspective side view of an alternative embodiment of the spinal fusion implant of the present invention.

Referring to FIG. 18, an alternative embodiment of the spinal fusion implant of the present invention is shown and generally referred to by the numeral 1000. The spinal fusion implant 1000 is similar to the spinal fusion implant 900, but has a narrower width such that more than one spinal fusion implant 1000 may be combined in a modular fashion for insertion within the disc space D between the adjacent vertebrae.

Figure 19:
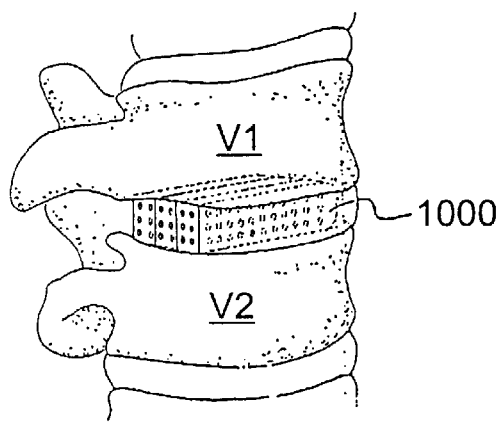
FIG. 19 is a perspective lateral anterior view of a segment of the spinal column with a plurality of the spinal implants of FIG. 18 shown in hidden line inserted from the lateral aspect in a modular fashion in the disc space between two adjacent vertebrae along the transverse width of the vertebrae.

Referring to FIG. 19, a plurality of spinal fusion implants 1000 are shown combined in a modular fashion inserted in the disc space D from the lateral aspect of the spine and along the transverse width of the vertebrae $V_1$ and $V_2$.

Figure 20:
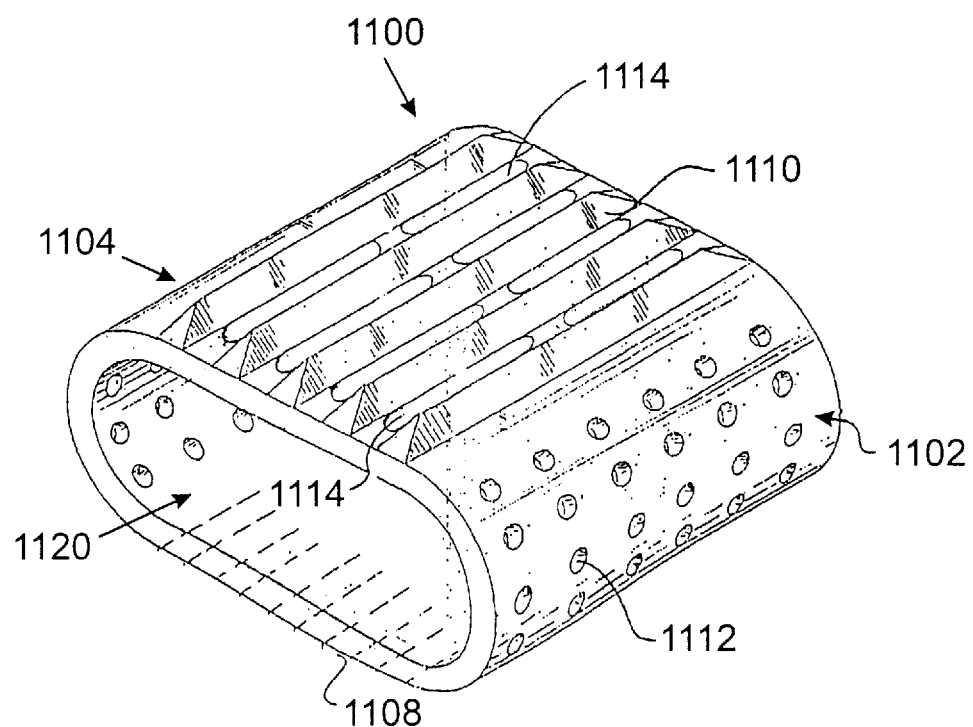
FIG. 20 is perspective view of an alternative embodiment of the spinal fusion implant of the present invention.

Referring to FIG. 20, an alternative embodiment of the spinal fusion implant of the present invention is shown and generally referred to by the numeral 1100. The spinal fusion implant 1100 is inserted into the disc space between two adjacent vertebrae from the lateral aspect of the spine and along the transverse width of the vertebrae. The implant 1100 is dimensioned to replace the natural disc material present between two adjacent vertebrae. The implant 1100 has a generally rectangular body with curved sides 1102 and 1104. The top and bottom surfaces 1106 and 1108 have a plurality of splines 1110 similar in structure and function as the splines 810 described above. As the implant 1100 is inserted in the disc space, the splines 1110 engage the bone of the adjacent vertebrae.

The implant 1100 is shown as being hollow with openings and slots 1114 in the outer surface of the implant 1100 permitting bone ingrowth into the interior of the implant 1100. However, it is appreciated that the implant 1100 may be solid and may have channels or wells in place of opening 1112 to permit bone ingrowth and incorporation of the implant 1100 into the spinal fusion mass. The interior of the implant 1000 may be accessed through the aperture 1120 which may be closed with a snap fit cover.

While the present invention has been described in detail with regards to the preferred embodiment, it is appreciated that other variations of the present invention may be devised which do not depart from the inventive concept of the present invention.

What is claimed is:

1. A translateral spinal implant for insertion from the lateral aspect of the spine in the disc space between two adjacent vertebrae, said implant having a length that is greater than one half the transverse width of the vertebrae, said length being substantially greater than the depth of the vertebrae, and a height for contacting each of the two adjacent vertebrae.

2. The spinal implant of claim 1 in which said implant has a height that is greater than the disc space and is capable of engaging both of said vertebrae.

3. The spinal implant of claim 1 in which said implant has surface roughenings for engaging said two adjacent vertebrae and for maintaining said implant in place, said surface roughenings being present on at least a portion of the exterior of said implant.

4. The spinal implant of claim 3, in which said surface roughenings include a plurality of ratchetings.

5. The spinal implant of claim 4, in which said ratchetings face one direction.

6. The spinal implant of claim 3, in which said surface roughenings include knurling.

7. The implant of claim 6 in which said implant has a cap on at least one end for removably closing said hollow portion of said Implant.

8. The spinal implant of claim 4 in which said surface roughenings include a plurality of longitudinal splines.

9. The spinal implant of claim 1 having a plurality of openings capable retaining fusion promoting material.

10. The spinal implant of claim 1 in which one end of said implant includes an engagement means for engaging instrumentation for the insertion of said implant.

11. The spinal implant of claim 1 in which said implant comprises a fusion promoting material.

12. The spinal implant of claim 1 in which said implant is at least in part bioabsorbable.

13. The spinal implant of claim 1 in which said implant has an internal chamber and an access opening for accessing said internal chamber.

14. The spinal implant of claim 13 in which said implant has means for closing said access opening.

15. The spinal implant of claim 13, in which said internal chamber is capable of containing fusion promoting material.

16. The spinal implant of claim 13, in which said implant comprises a wall surrounding at least in part said internal chamber.

17. The spinal implant of claim 16, in which said wall has a plurality of openings passing therethrough in communication with said internal chamber.

18. The implant of claim 1 in which said implant includes driving engaging means for engaging a driving instrument for implanting said implant within the disc space between the two adjacent vertebrae.

19. The implant of claim 1 in which said implant is generally rectangular in shape.

20. The implant of claim 1 in which said implant is generally square in shape.

21. The implant of claim 1 which said implant comprises a plurality of modular members, each of said modular members having a length that is greater than one half the transverse width of the vertebrae, said length being substantially greater than the depth of the vertebrae, a height dimensioned to fit in the space created by the removed disc material from between two adjacent vertebrae, and a width less than the depth of the vertebrae.

22. The spinal implant of claim 21 in which said implant has a height that is greater than the disc space and is capable of engaging both of said vertebrae.

23. The spinal implant of claim 1 in which said implant comprises a bone ingrowth material.

24. The implant of claim 1 for use in the lumbar spine in which the length of said implant is in the range of approximately 35 mm to 50 mm.

25. The implant of claim 1 for use in the thoracic spine in which the length of said implant is in the range of approximately 12 mm to 30 mm.

26. The spinal implant of claim 1 in which said implant has a height that is greater than the disc space and is capable of penetrating into each of the two adjacent vertebrae.

27. The spinal implant of claim 26 in which said implant is at least in part cylindrical in shape.

28. The spinal implant of claim 27, in which said implant has an external thread for engaging the vertebrae.

29. The spinal implant of claim 27, in which said implant is hollow.

30. The implant of claim 27, for use in the lumbar spine in which the diameter of said implant is in the range of approximately 22 mm to 30 mm.

31. The implant of claim 27, for use in the thoracic spine in which the diameter of said implant is in the range of approximately 14 mm to 26 mm.

32. The implant of claim 27, for use in the lumbar spine in which said implant has a length in the range of approximately 38 mm to 44 mm and diameter in the range of approximately 24 mm to 30 mm.

33. The implant of claim 27, for use in the thoracic spine in which said implant has a length in the range of approximately 12 mm to 30 mm and diameter in the range of approximately 14 mm to 26 mm.

34. A translateral spinal implant for insertion from the lateral aspect of the spine in the disc space between two adjacent vertebrae, comprising:

a plurality of modular members, each of said modular members having a length that is greater than one half the transverse width of the vertebrae, said length being substantially greater than the depth of the vertebrae, a width less than the depth of the vertebrae, and a height for contacting each of the two adjacent vertebrae, each of said modular members comprising:

upper and lower walls, and side walls, said upper and lower walls forming a support structure including at least a portion of the interior surface of said upper and lower walls for bearing against the end plates of the adjacent vertebrae, whereby said plurality of modular members are capable of being inserted in between said two adjacent vertebrae.

35. A translateral spinal implant for insertion from the lateral aspect of the spine in the disc space between two adjacent vertebrae, said implant having a length that is greater than one half the transverse width of the vertebrae, said length being substantially greater than the depth of the vertebrae, a height for contacting each of the two adjacent vertebrae, and a width that is at least as great as the height.

36. The spinal implant of claim 35 in which said implant has a height that is greater than the disc space and is capable of engaging both of said vertebrae.

37. The spinal implant of claim 36, in which said implant is at least in part cylindrical in shape.

38. The spinal implant of claim 37, in which said implant has an external thread for engaging the vertebrae.

39. The spinal implant of claim 37, in which said implant is hollow.

40. The spinal implant of claim 35, in which said implant has surface roughenings for engaging said two adjacent vertebrae and for maintaining said implant in place, said surface roughenings being present on at least a portion of the exterior of said implant.

41. The spinal implant of claim 40 in which said surface roughenings include a plurality of ratchetings.

42. The spinal fusion implant of claim 41, in which said ratchetings face one direction.

43. The spinal implant of claim 40, in which said surface roughenings include knurling.

44. The implant of claim 43, in which said implant has a cap on at least one end for removably closing said hollow portion of said Implant.

45. The spinal implant of claim 40, in which said surface roughenings include a plurality of longitudinal splines.

46. The spinal implant of claim 35, having a plurality of openings capable retaining fusion promoting material.

47. The spinal implant of claim 35, in which one end of said implant includes an engagement means for engaging instrumentation for the insertion of said implant.

48. The spinal implant of claim 35, in which said implant comprises a fusion promoting material.

49. The spinal implant of claim 35 in which said implant is at least in part bioabsorbable.

50. The spinal implant of claim 35 in which said implant has an internal chamber and an access opening for accessing said internal chamber.

51. The spinal implant of claim 50, in which said implant has means for closing said access opening.

52. The spinal implant of claim 50 in which said internal chamber is capable of containing fusion promoting material.

53. The spinal implant of claim 50, in which said implant comprises a wall surrounding at least in part said internal chamber.

54. The spinal implant of claim 53, in which said wall has a plurality of openings passing therethrough in communication with said internal chamber.

55. The implant of claim 35, which said implant comprises a plurality of modular members, each of said modular members having a length that is greater than one half the transverse width of the vertebrae, said length being substantially greater than the depth of the vertebrae, a height to the height of the space created by the removed disc material from between two adjacent vertebrae, and a width substantially less than the depth of the vertebrae.

56. The spinal implant of claim 55 in which said implant has a height that is greater than the disc space.

57. The implant of claim 35 in which said implant is generally rectangular in shape.

58. The implant of claim 35, in which said implant includes driving engaging means for engaging a driving instrument for implanting said implant within the disc space between the two adjacent vertebrae.

59. The spinal implant of claim 35, in which said implant comprises a bone ingrowth material.

60. The implant of claim 35, in which said implant is generally square in shape.

61. A translateral spinal fusion implant for insertion from the lateral aspect of the spine in the disc space between two adjacent vertebrae, said implant having a length that is greater than one half the transverse width of the vertebrae, said length being substantially greater than the depth of the vertebrae, and a height for contacting each of the two adjacent vertebrae; said implant having an outer surface with a plurality of openings passing through said implant, said plurality of openings capable of retaining fusion promoting substances and capable of permitting bone growth in continuity from one of said adjacent vertebrae to the other of said two adjacent vertebrae to permit fusion of said two adjacent vertebrae to occur at least in part through said implants capable of engaging both of said vertebrae.

62. The spinal implant of claim 1 in which said implant is made of an artificial material.

63. The spinal implant of claim 34 in which said implant is made of an artificial material.

64. The spinal implant of claim 35 in which said implant is made of an artificial material.

65. The spinal implant of claim 61 in which said implant is made of an artificial material.

66. The spinal implant of claim 1 in which said implant comprises bone morphogenetic protein.

67. The spinal implant of claim 34 in which said implant comprises bone morphogenetic protein.

68. The spinal implant of claim 35 in which said implant comprises bone morphogenetic protein.

69. The spinal implant of claim 61 in which said implant comprises bone morphogenetic protein.

70. The spinal implant of claim 1 in which said implant comprises a bioactive material.

71. The spinal implant of claim 34 in which said implant comprises a bioactive material.

72. The spinal implant of claim 35 in which said implant comprises a bioactive material.

73. The spinal implant of claim 61 in which said implant comprises a bioactive material.

* * * * *

UNITED STATES PATENT AND TRADEMARK OFFICE
CERTIFICATE OF CORRECTION

PATENT NO. : 5,860,973
DATED : January 19, 1999
INVENTOR(S) : Gary Karlin Michelson It is certified that error appears in the above-identified patent and that said Letters Patent is hereby corrected as shown below:

Column 12, claim 34,
Line 13, change "interior" to -- exterior --.

Signed and Sealed this

Sixteenth Day of April, 2002

Attest:

JAMES E. ROGAN
Attesting Officer — Director of the United States Patent and Trademark Office